(12) United States Patent
Eda

(10) Patent No.: US 12,121,396 B2
(45) Date of Patent: Oct. 22, 2024

(54) PROBE HOLDER

(71) Applicant: FUJIFILM Healthcare Corporation, Kashiwa (JP)

(72) Inventor: Masato Eda, Chiba (JP)

(73) Assignee: FUJIFILM Corporation, Tokyo (JP)

(*) Notice: Subject to any disclaimer, the term of this patent is extended or adjusted under 35 U.S.C. 154(b) by 274 days.

(21) Appl. No.: 17/748,545

(22) Filed: May 19, 2022

(65) Prior Publication Data
US 2022/0378398 A1 Dec. 1, 2022

(30) Foreign Application Priority Data
May 27, 2021 (JP) .................................. 2021-089047

(51) Int. Cl.
*A61B 50/20* (2016.01)
*A61B 8/00* (2006.01)

(52) U.S. Cl.
CPC ............ *A61B 8/4209* (2013.01); *A61B 50/20* (2016.02)

(58) Field of Classification Search
CPC ..... A61B 8/4209; A61B 50/20; A61B 8/4405; A61B 50/22; A47G 23/0633; A47F 7/0028
USPC ... 211/85.13, 119.005, 85.18, 70.6, 66, 69.5, 211/63, 70.8; 248/311.3, 314
See application file for complete search history.

(56) References Cited

U.S. PATENT DOCUMENTS

| | | | |
|---|---|---|---|
| 1,584,101 A * | 5/1926 | Kovarik | A47G 25/12 211/63 |
| 3,136,426 A * | 6/1964 | Yasuji | A47G 25/12 D6/680.2 |
| 3,463,323 A * | 8/1969 | Riepe | B43M 99/007 D19/135 |
| 3,955,682 A * | 5/1976 | Baren | B01L 9/00 211/74 |
| 4,155,460 A * | 5/1979 | Ratti | B25H 3/003 211/70.6 |
| 4,253,830 A * | 3/1981 | Kazen | A61C 3/04 206/379 |
| 4,271,878 A * | 6/1981 | Bologa | B67C 9/00 D7/619.1 |
| 4,341,312 A * | 7/1982 | Scholer | A61C 3/04 211/70.6 |
| 5,033,629 A * | 7/1991 | Caine | B43M 99/007 211/69.5 |
| 5,378,433 A * | 1/1995 | Duckett | B01L 9/06 206/443 |

(Continued)

FOREIGN PATENT DOCUMENTS

| | | | | |
|---|---|---|---|---|
| JP | 2000333949 A | * | 12/2000 | |
| JP | 2004053588 A | * | 2/2004 | ............... A61B 8/00 |

(Continued)

OTHER PUBLICATIONS

Jan. 16, 2024 Japanese official action (machine translation into English) in connection with Japanese Patent Application No. 2021-089047.

*Primary Examiner* — Jennifer E. Novosad

(74) *Attorney, Agent, or Firm* — Paul Teng

(57) ABSTRACT

A probe holder includes a casing and an elastic structure including an inner cover and a retainer unit. The retainer unit includes an enclosing wall, and a rib array protruding from an inner face of the enclosing wall. The rib array holds a cable end with a rear end of a probe head being supported by a support face of the inner cover.

7 Claims, 7 Drawing Sheets

(56) References Cited

U.S. PATENT DOCUMENTS

| | | | | |
|---|---|---|---|---|
| 5,673,696 A * | 10/1997 | Bidwell | ............... | G10K 11/004 600/437 |
| D391,838 S * | 3/1998 | Bidwell | ............ | D8/356 |
| 5,979,675 A * | 11/1999 | Moriarty | ............... | B01L 9/54 248/231.71 |
| 5,985,219 A * | 11/1999 | Lind | ............... | B01L 9/06 422/562 |
| 6,220,458 B1 * | 4/2001 | Falor | ............... | A47G 23/0241 211/74 |
| 6,345,722 B1 * | 2/2002 | Wingate | ............ | A63B 71/0036 473/282 |
| 6,481,583 B1 * | 11/2002 | Black | ............... | A47F 5/0815 211/89.01 |
| 6,626,402 B1 * | 9/2003 | Kaminstein | ............ | A46B 17/02 248/314 |
| 7,219,464 B1 * | 5/2007 | Kujawa | ............ | A01K 97/08 211/8 |
| D554,264 S * | 10/2007 | Watson | ............ | D24/186 |
| 7,896,173 B2 * | 3/2011 | Yamamoto | ............ | A47B 81/005 211/70.2 |
| 7,910,067 B2 * | 3/2011 | Knight | ............ | B01L 9/06 422/562 |
| 8,132,681 B2 * | 3/2012 | Afghan | ............ | A47K 1/09 211/66 |
| 8,141,719 B2 * | 3/2012 | Hopper | ............ | A47F 7/0028 211/163 |
| 8,550,550 B2 * | 10/2013 | Cassese | ............ | B65D 15/00 220/23.8 |
| 8,789,713 B2 * | 7/2014 | Koller | ............ | A47F 7/0028 211/74 |
| 8,810,076 B2 * | 8/2014 | Levi | ............ | A45D 20/14 312/204 |
| 8,887,929 B2 * | 11/2014 | Erlenbach | ............ | A47F 5/0006 248/690 |
| 8,911,233 B2 * | 12/2014 | Moore | ............ | A47F 7/0028 433/163 |
| 11,278,373 B2 * | 3/2022 | Zieris | ............ | A61B 50/30 |
| 2003/0215370 A1 * | 11/2003 | Itoh | ............ | B01L 9/06 422/400 |
| 2003/0236463 A1 | 12/2003 | Mesaros et al. | | |
| 2005/0145585 A1 * | 7/2005 | Pintar | ............ | A47B 81/005 211/96 |
| 2006/0097121 A1 * | 5/2006 | Fugate | ............ | A47G 23/0309 248/311.2 |
| 2006/0284041 A1 * | 12/2006 | Segretto | ............ | A47G 23/0225 248/311.2 |
| 2007/0193965 A1 * | 8/2007 | Cialdella | ............ | A63B 55/00 211/70.2 |
| 2014/0259604 A1 | 9/2014 | Romano et al. | | |
| 2022/0378398 A1 * | 12/2022 | Eda | ............ | A61B 50/20 |

FOREIGN PATENT DOCUMENTS

| | | | | |
|---|---|---|---|---|
| JP | 2005-168885 A | | 6/2005 | |
| JP | 2005-287915 A | | 10/2005 | |
| JP | 2011-139722 A | | 7/2011 | |
| JP | 2011-244996 A | | 12/2011 | |
| JP | 2015136464 A | * | 7/2015 | |
| JP | 2016-209082 A | | 12/2016 | |
| JP | 2019-126454 A | | 8/2019 | |
| JP | 2022180989 A | * | 12/2022 | |
| JP | 2022181856 A | * | 12/2022 | ........... A61B 8/4209 |

\* cited by examiner

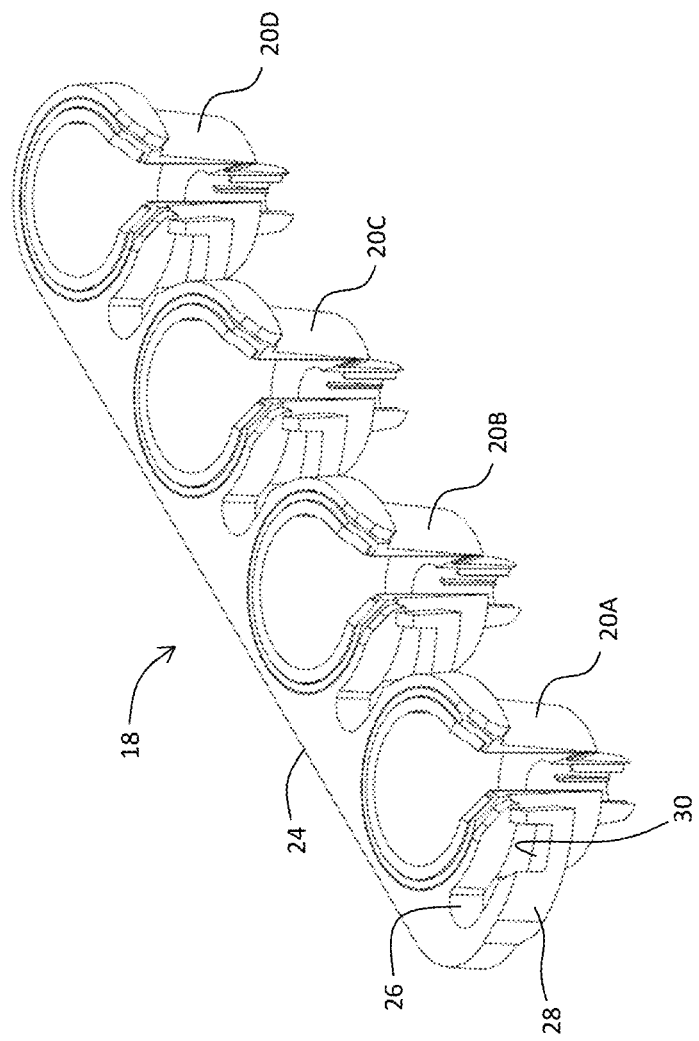

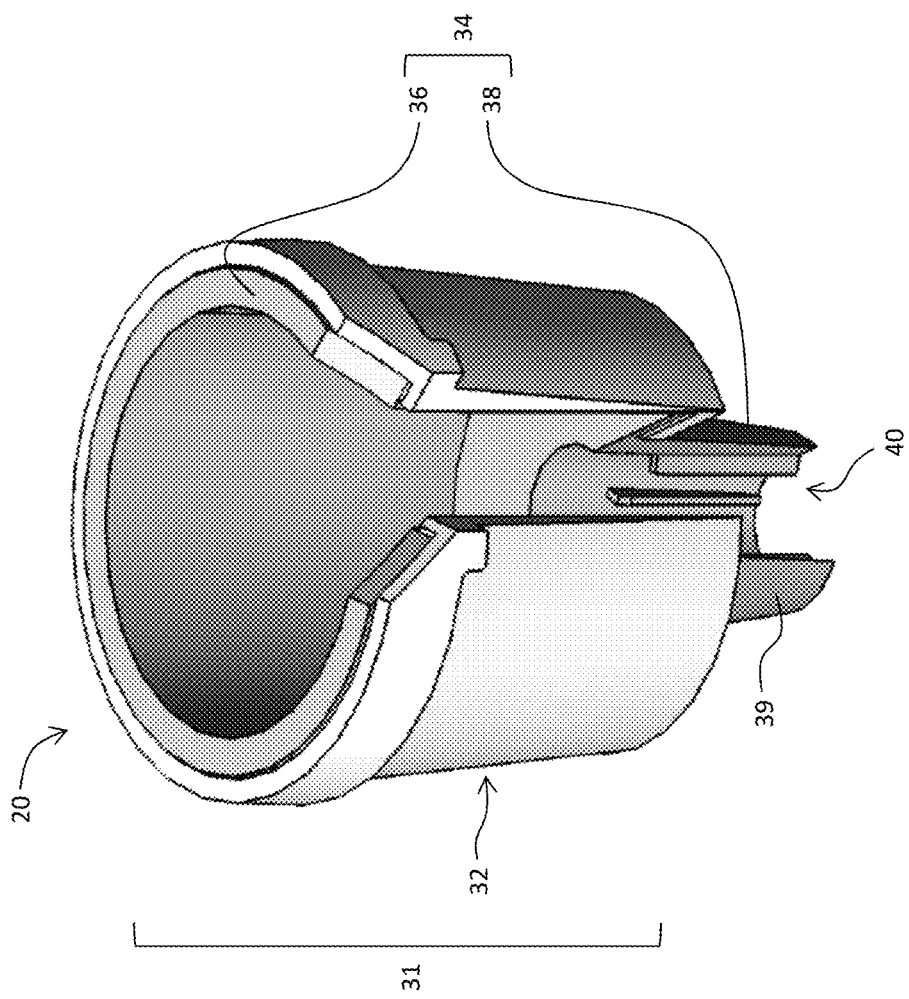

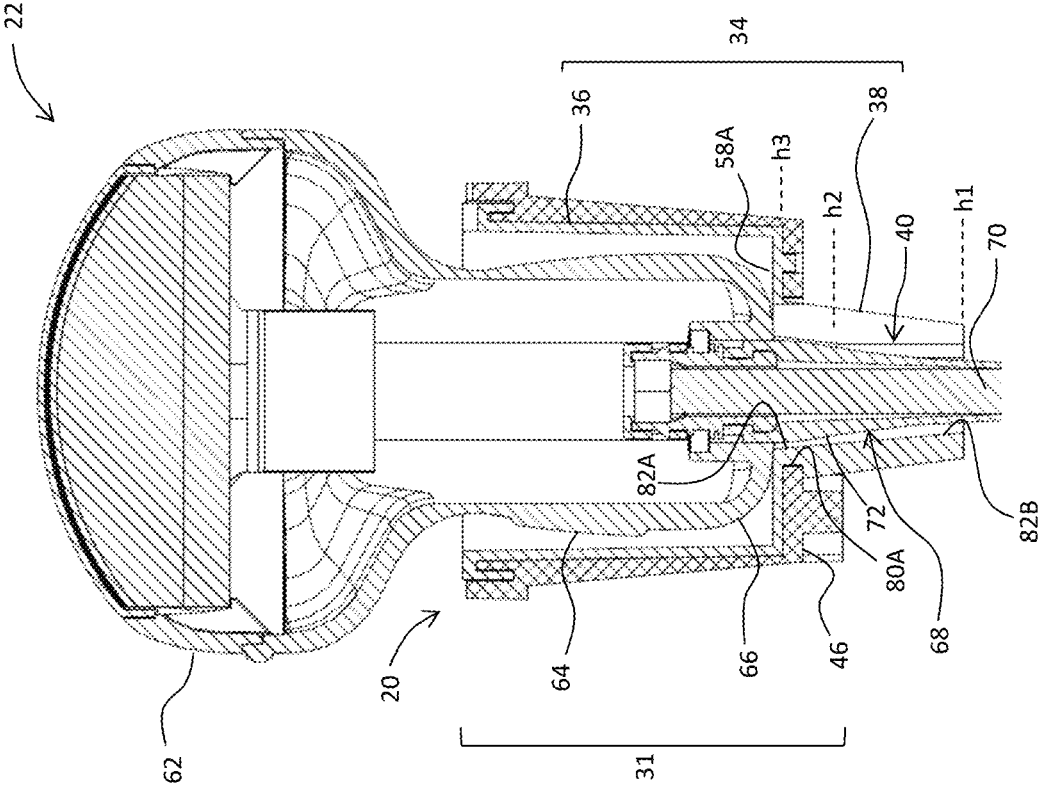

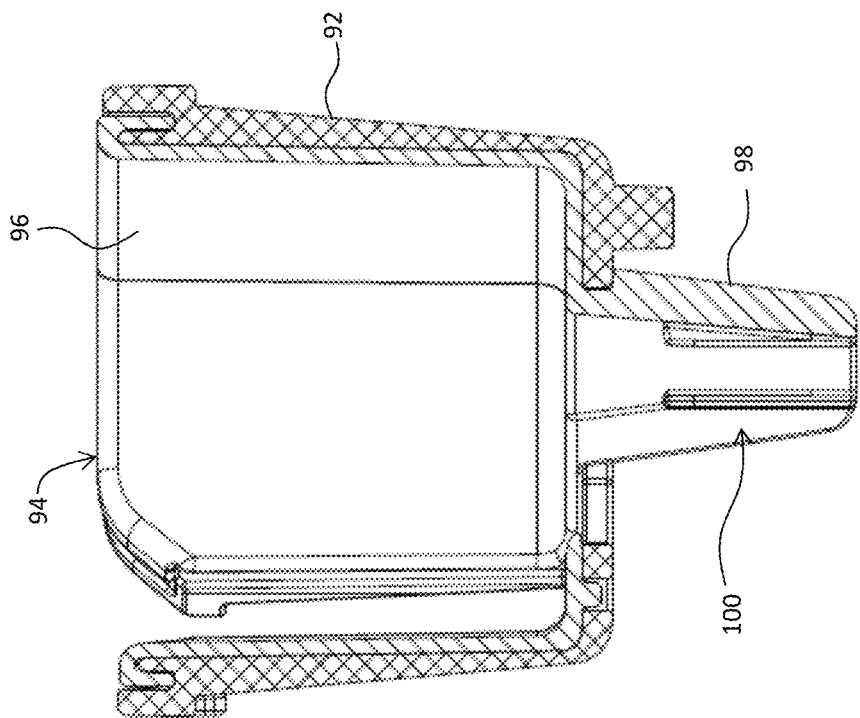
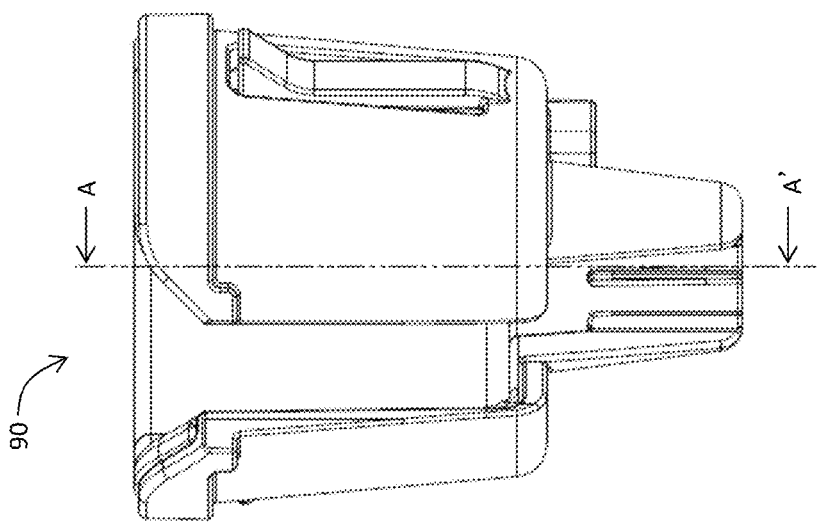

PROBE HOLDER

CROSS REFERENCE TO RELATED APPLICATION

This application claims priority to Japanese Patent Application No. 2021-089047 filed on May 27, 2021, which is incorporated herein by reference in its entirety including the specification, claims, drawings, and abstract.

TECHNICAL FIELD

The present disclosure relates to a probe holder, and more particularly to a structure of a probe holder.

BACKGROUND

Ultrasonic diagnostic apparatuses typically include a probe holder unit. A probe holder unit is an assembly of a plurality of probe holders individually holding probes. Specifically, a probe includes a probe head, a cable, and a connector, and the connector is detachably coupled to an ultrasonic diagnostic apparatus body. After a probe is used, the probe head is placed in an upright position, and the probe head in this state is fitted into a storage space in the probe holder unit and is held by one of the probe holders.

Document 1 (JP 2015-136464 A) discloses a probe holder having a plurality of protrusions to hold a grip portion (intermediate portion) of a probe head that is in an upright position. Document 1 nowhere discloses a structure that acts on a cable extending from the probe head in order to keep the upright position of the probe head. Document 2 (JP 2005-168885 A) discloses an ultrasonic probe including a coating having a luminous material.

SUMMARY

Probe heads may have various sizes and shapes. However, a probe holder including a complicated structure to securely hold a variety of probe heads would raise a problem of increased costs.

Embodiments of the disclosure are therefore directed toward providing a probe holder with a simple configuration that enables secure holding of various probes.

In accordance with an aspect of the disclosure, a probe holder includes a holder body having a support face configured to support a rear end of a probe head that is in an upright position, and a retainer unit disposed under the holder body and configured to hold a cable end connecting to the rear end of the probe head to maintain the upright position of the probe head with the rear end of the probe head being supported by the support face.

BRIEF DESCRIPTION OF DRAWINGS

Embodiments of the present disclosure will be described based on the following figures, wherein:

FIG. 2 is a perspective view of a probe holder unit;

FIG. 3 is a perspective view of a probe holder;

FIG. 6 is a cross sectional view illustrating the probe holder holding a probe;

FIG. 8 is a front view of the probe holder according to the modification example; and FIG. 9 is a cross sectional view of the probe holder according to the modification example.

DESCRIPTION OF EMBODIMENTS

Figure 1:
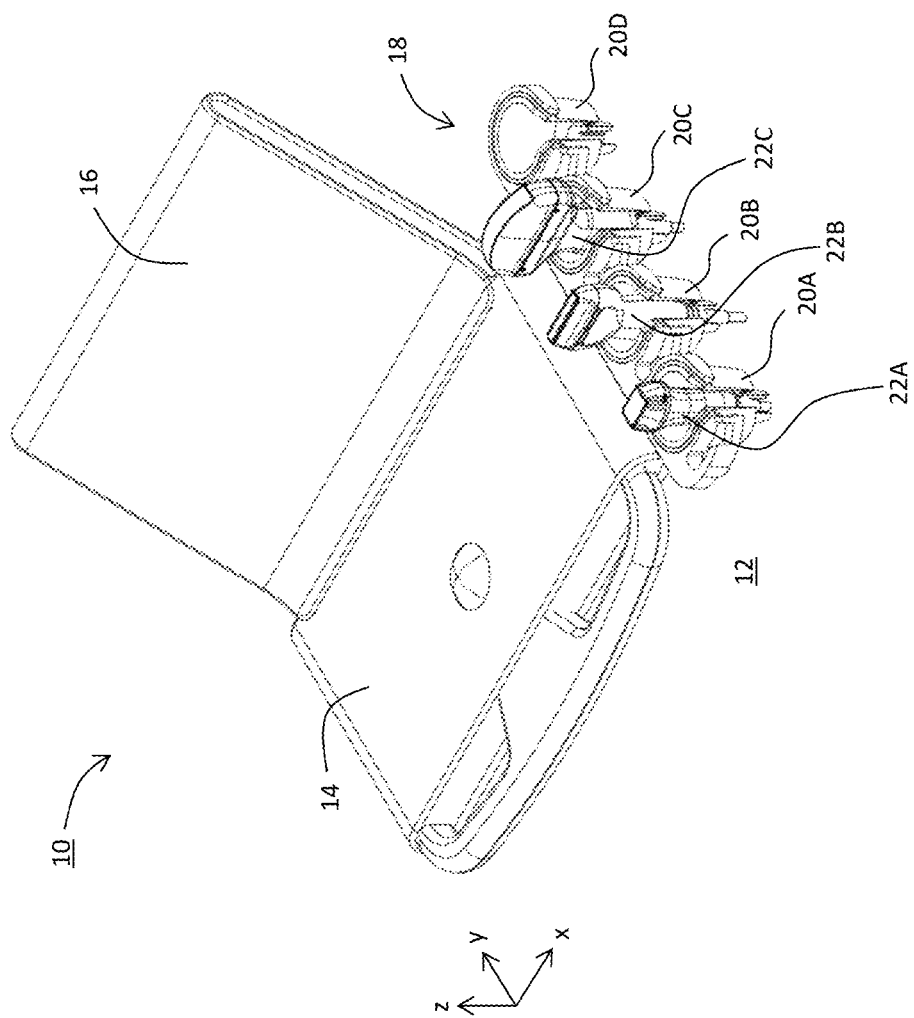
FIG. 1 is a perspective view illustrating an ultrasonic diagnostic apparatus according to an embodiment.

Embodiments of the disclosure will be described by reference to the drawings.

(1) Summary of Embodiments

A probe holder according to an embodiment includes a holder body and a retainer unit. The holder body includes a support face that supports a rear end of a probe head that is in an upright position. The retainer unit is disposed under the holder body, and holds a cable end connecting to the rear end of the probe head to keep the upright position of the probe head with the rear end of the probe head being supported on the support face of the holder body.

The above configuration of the probe holder allows the support face to receive the load of the probe head and the like and allows the retainer unit to hold the cable end connecting to the rear end of the probe head, thereby keeping the upright position of the probe head. Probe heads typically have various different shapes and different sizes. Meanwhile, probe ends do not have such a variety of shapes or sizes; therefore, the shapes or sizes of the probe ends are somewhat similar. The probe holder described above therefore retains the cable end extending from the probe head to thereby securely hold a probe irrespective of the size or shape of its probe head, by means of a relatively simple configuration.

The cable end of a probe typically includes a protection member having a predetermined rigidity that is connected to the rear end of the probe head. In an embodiment, this protection member is retained by the retainer unit. When the probe head is caused to move in a slant direction with the cable end being retained, the cable end would attempt to move in an opposite slant direction. At this time, the retainer unit applies to the cable end resistance to restore the upright state (vertical position) of the probe head.

Probe holders widely used typically have a structure that surrounds the probe head such as its body portion, for example. The above configuration, however, can hold a probe without such a structure. However, the probe holder may include a structure that surrounds the probe head to provide a physical guard for the probe head, to restrict a movement in case of slanting movement of the probe head, or to provide visual safety, for example.

In an embodiment, the cable end includes a cable boot surrounding a cable body, and the retainer unit holds the cable boot. The cable boot is a protection member that is more rigid than the cable body and increases the rigidity of the cable end. As the cable boot is normally coupled directly to the probe head, externally holding the cable boot provides a sufficient force to retain the position of the probe head.

In an embodiment, the retainer unit includes an enclosing wall protruding downward from the holder body, and a plurality of projections protruding from an inner face of the enclosing wall to come into elastic contact with an outer face of the cable end. The plurality of elastic projections maintain a desirable holding state of the probe in response to a change in the size or shape of the cable end. Three or more projections facilitate positioning of the center axis of the cable end to the center axis of the retainer unit.

In an embodiment, the holder body includes an upper slit extending vertically to allow the cable to pass through. The enclosing wall of the retainer unit includes a lower slit connecting to the upper slit and extending vertically to allow the cable to pass through. In an embodiment, the enclosing wall has two edges defining the lower slit. Each projection is a rib extending vertically and protruding toward the center axis of the retainer unit. The plurality of ribs or the plurality of projections include two ribs disposed close to the two edges. This configuration effectively prevents the cable from being naturally removed from the retainer unit. Holding force of the retainer unit may be adjusted by adjusting the protruding amount and elasticity of each rib.

In an embodiment, the holder body includes a hollow casing, and an inner cover having a support face and covering the inner face of the casing. This configuration avoids direct contact between the casing and the probe head to thereby protect the probe head. In an embodiment, the inner cover is integral with the retainer unit to form an elastic structure. This configuration reduces the number of components and achieves cost reduction.

In an embodiment, the elastic structure includes a luminous material. During the ultrasonic inspection, the inspection room is typically darkened for the convenience of observation of ultrasound images. The elastic structure which itself emits light makes the location and shape of the probe holder noticeable, to thereby facilitate removal of the probe head from the probe holder and mounting of the probe head on the probe holder.

In an embodiment, at least one of the holder body and the retainer unit partially includes a luminous material. The probe holder without a structure for holding the cable end may partially or entirely include a material containing a luminous material. For example, such a probe holder may include a coating film containing a luminous material or a component having a luminous material.

(2) Details of Embodiments

FIG. 1 illustrates an ultrasonic diagnostic apparatus 10 according to an embodiment. The ultrasonic diagnostic apparatus 10 is a medical device that forms ultrasound images based on reception data obtained by transmission and reception of ultrasound waves with respect to a living body (subject) and is used in medical facilities. In FIG. 1, the x-direction indicates a lateral direction along the width of the apparatus, the y-direction indicates a forward-rearward direction along the depth of the apparatus, and the z-direction indicates a vertical direction along the height of the apparatus.

The ultrasonic diagnostic apparatus 10 is a push-cart ultrasonic diagnostic apparatus. The ultrasonic diagnostic apparatus 10 includes an apparatus body 12 that is not illustrated. The apparatus body 12 has a box shape and has a plurality of castors at its lower part. The apparatus body 12 supports, via a support mechanism that is not illustrated, an operation panel 14 that is an input device having a plurality of buttons, a plurality of knobs, a track ball, and a keyboard, for example.

A display 16 is disposed further backward of the operation panel 14. The display 16 may be supported by the operation panel 14 via an arm mechanism. The display 16 may be an organic EL display or an LCD, for example, and displays ultrasound images. The operation panel 14 includes a handle on a front side.

A probe holder unit 18 is disposed on a right side of the operation panel 14; however, the probe holder unit 18 may be disposed on a left side of the operation panel 14. The probe holder unit 18 has a plurality of probe holders 20A to 20D that hold four or fewer probes.

The probes include probe heads 22A to 22C, respectively, and each probe includes a cable and a connector. Each of the probe heads 22A to 22C includes a transducer array including a plurality of transducers. The transducer array forms ultrasound beams for electronic scanning. Known electronic scanning methods include electronic linear scan and electronic sector scan, for example. The probe heads 22A to 22C may have different shapes and different sizes in accordance with different scanning methods and inspection targets. Meanwhile, the cables extending from the respective probe heads 22A to 22C have substantially the same shape and size. Each cable has an end (connection end) coupled with a rear end of each of the probe heads 22A to 22C. The probe holder unit 18 may include a single probe holder, and may further include a device such as a jelly warmer.

FIG. 2 is an enlarged perspective view of the probe holder unit 18. The probe holder unit 18 includes a frame 24 and the four probe holders 20A to 20D. The frame 24 is formed from aluminum, for example. The probe holders 20A to 20D have a casing (outer wall) made of hard resin, for example. The frame 24 and the probe holders 20A to 20D may be integrally formed. The four probe holders 20A to 20D having the same shape are arranged along the depth direction.

An arm 28 is disposed in front of each of the probe holders 20A to 20D, via a corresponding slot 26. The arms 28 are part of the frame 24. Each arm 28 includes a cable hook 30, and the slot 26 functions as a channel that receives the cable.

FIG. 3 is a perspective view of the probe holder 20 including a holder body 31 and a retainer unit 38. The retainer unit 38 is disposed under the holder body 31 to protrude downward.

The holder body 31 includes a casing 32 and an inner cover 36. The casing 32 is a hollow container or cup and includes an inner face entirely covered with the inner cover 36. The inner cover 36 and the retainer unit 38 integrally form a single elastic structure 34. In other words, the probe holder 20 is formed of the casing 32 and the elastic structure 34. The casing 32 is harder than the elastic structure 34, and is specifically made of a hard resin. The holder body 31 has a support face or a seat face that supports the rear end of the probe head in an upright position, as will be described below.

The retainer unit 38 is a cable holder that holds a cable end connecting to the rear end of the probe head. The retainer unit 38 includes an enclosing wall 39 and a rib array 40. The enclosing wall 39 has a substantially cylinder shape (having a C horizontal cross section) and has an inner face on which the rib array 40 is disposed. In the illustrated example, the rib array 40 includes four ribs, each protruding from the inner face of the enclosing wall 39 toward the center axis of the retainer unit 38.

In the embodiment, the elastic structure 34 is made of an elastic material such as silicone rubber, and the elastic material contains a luminous material. Alternatively, the elastic structure 34 is coated with a luminous material. Various luminous materials are known, including an $SrAl_2O_4$-based luminous material and a ZnS-based luminous material, for example. The elastic structure 34 containing a luminous material emits light when the inspection room is darkened, thereby facilitating insertion of the probe into the probe holder 20 or removal of the probe from the probe holder 20. This configuration particularly facilitates insertion or removal of the cable into or from the slits in the probe holder 20. A desired emission color can be selected by selecting a luminous material.

Figure 4:
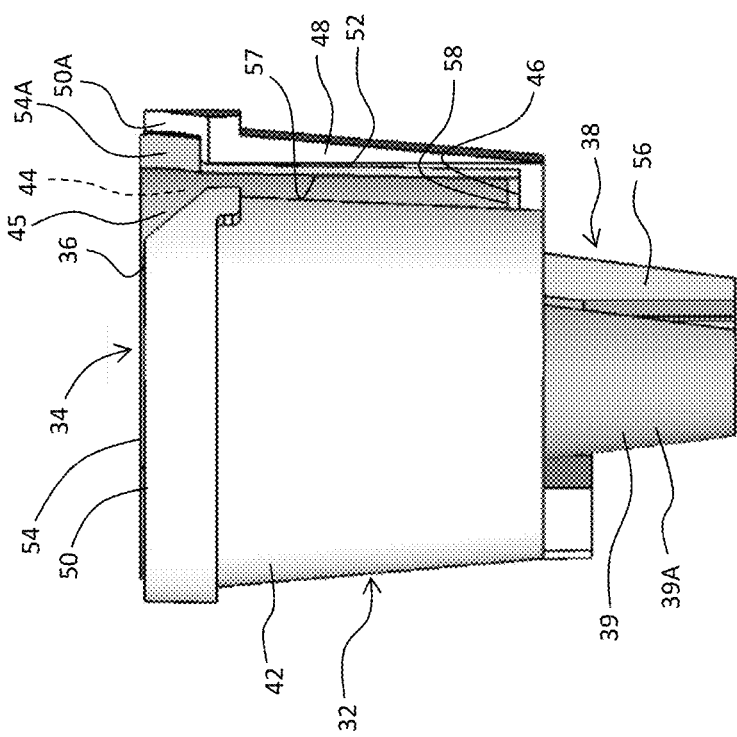
FIG. 4 is a front view of the probe holder.

FIG. 4 is a front view of the probe holder. The casing 32 has a cup shape having a bottom wall 46 with an opening in the center to allow the retainer unit 38 to protrude downward. The casing 32 includes a cylindrical casing body 42 including a large-thickness upper portion. The top face of the large-thickness upper portion is indicated with numeral 50. The casing 32 has a vertical slit 48.

The elastic structure 34 includes the inner cover 36 that covers the entire inner face of the casing 32, and the retainer unit 38. The inner cover 36 includes a cylindrical portion 57, and a rim portion 54 expanding horizontally on the upper edge of the cylindrical portion 57. The rim portion 54 partially covers the annular top face 50 of the casing 32. The inner space of the casing 32 is indicated by reference numeral 44, and the inner space of the inner cover 36 is indicated by reference numeral 45.

The inner cover 36 has the bottom wall 58 having in its center an opening to allow the cable to pass through. The inner cover 36 further includes a slit 52 extending vertically. The slit 48 in the casing 32 and the slit 52 in the inner cover 36 form an upper slit that functions as a passage channel for the cable. The casing 32 further includes a pair of slope faces 50A above the upper portion of the slit 48. The inner cover 36 further includes a pair of slope faces 54A along the pair of slope face 50A above the slit 52.

The enclosing wall 39 of the retainer unit 38 has a tapered shape having a gradually decreasing diameter from its top toward the bottom. The enclosing wall 39 has a conical outer face 39A. The enclosing wall 39 includes a vertical slit 56 that functions as the lower slit connecting to the upper slit. The enclosing wall 39 has an interior that is a cable retaining space opened at its top and bottom.

Figure 5:
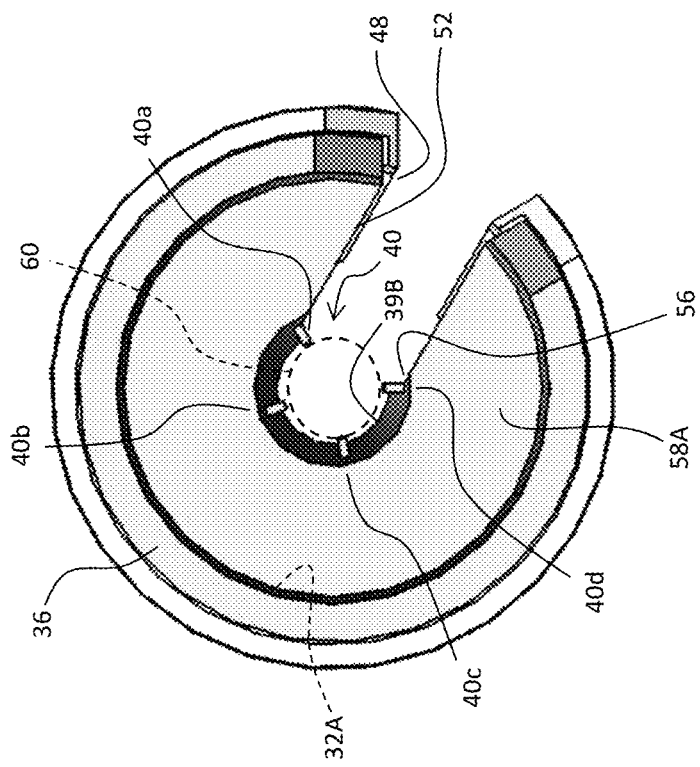
FIG. 5 is a top view of the probe holder.

FIG. 5 is a top view of the probe holder. The casing inner face 32A is entirely covered with the inner cover 36. The inner cover 36 has a cylindrical portion and a bottom wall, and the top face of the bottom wall functions as a support face 58A that supports the rear end of the probe head in the upright position. As described above, the slit 48 and the slit 52 form the upper slit.

As described above, the inner face 39B of the enclosing wall has the rib array 40 in the retainer unit. The rib array 40 includes four ribs 40a to 40d, of which the rib 40a and the rib 40d are disposed close to two edges defining the slit 56 in the retainer unit. Tip end portions of the four ribs 40a to 40d come into elastic contact with the outer face of a cable 60 (more specifically, the outer face of the cable boot). The four ribs 40a to 40d hold the cable 60, with the center axis of the cable 60 being aligned with the center axis of the retainer unit.

When the probe head in an upright position is caused to move in a slant direction with the rear end of the probe head being supported on the support face 58A, the cable end is urged to move in the opposite slant direction. Resistance against this slanting movement acts on the cable end from the retainer unit to thereby maintain the vertical position of the probe head. Basically, any type of probe head, when inserted in the holder body, is not in contact with the holder body except the lower end face of the probe head, and thus the holder body does not basically provide an effect of retaining the probe head.

In the embodiment, in mounting the probe in the probe holder, the upper slit and the lower slit function as a cable passage. The two ribs 40a and 40d disposed close to the two edges defining the lower slit prevent removal of the cable from the lower slit. While the ribs 40a to 40d are non-hollow projections, the ribs may be hollow projections. The rib array 40 may include three ribs or may include five or more ribs. The ribs 40a to 40d are to be collapsed by an appropriate degree in accordance with the size of the cable 60 to thereby securely retain various cables of different sizes and shapes.

For example, each of the ribs 40a to 40d protrudes from the inner face 39B of the enclosing wall by an amount of 1.2 mm at a lower portion of each rib and by an amount of 4 mm at an upper portion of each rib. Some probes may have a cable end with an outer diameter that changes from 9 mm to 15 mm, for example. Different types of probes have different ranges of changes in the outer diameter of the cable end. The amount of protrusion of each rib is determined so as to securely hold the cable ends with outer diameters that may change as described above. The outer diameter of the cable body is within a range from 6 mm to 10 mm.

FIG. 6 is a cross sectional view illustrating a probe being held by the probe holder. The probe includes the probe head 22 and a cable 68. The probe head 22 includes a tip end 62, a body portion (grip portion) 64, and a rear end 66. The tip end 62 includes a transducer array including a plurality of transducers. In the illustrated example, the tip end 62 is enlarged as compared with the body portion 64. The cable 68 is extended from the rear end 66. FIG. 6 shows an end (a cable end) of the cable 68 connecting to the rear end 66 of the probe head 22.

The cable end includes a cable body 70, and a cable boot 72 surrounding the cable body 70. The cable boot 72 is a cover member that protects the end of the cable body 70 including a great number of signal lines. The cable boot 72 has a predetermined elasticity and is made of a resin or rubber material, for example. The cable boot 72 has an effect of increasing the rigidity of the cable end. The cable boot 72 has an increasing thickness from the bottom to the top and thus has an increasing outer diameter from the bottom to the top. The upper end of the cable boot 72 protrudes into the rear end 66 of the probe head 22 and mechanically couples with the rear end 66.

The holder body 31 stores the body portion 64 and the rear end 66 of the probe head 22. The tip end 62 of the probe head 22 protrudes from the probe holder 20 and is externally exposed. The elastic structure 34 includes the inner cover 36 and the retainer unit 38 that are integrally formed. The retainer unit 38 protrudes downward through an opening 80A of the bottom wall 46 of the casing. The retainer unit 38 has a cable holding space having an upper opening 82A and a lower opening 82B. The retainer unit 38 includes, on its inner face, the rib array 40 including a plurality of ribs annularly arranged to hold the cable 68. Each rib is a projection extending vertically.

The retainer unit 38 is formed over a range from a lower end lever h1 to an upper end level h3. In the embodiment, the rib array 40 is formed over a range from the lower end level h1 to an intermediate level h2. However, the rib array 40 may be formed over the entire range from the lower end level h1 to the upper level h3.

The support face 58A receives the load of the probe head 22, for example. The retainer unit 38 retains the cable 68 extending from the probe head 22 to thereby keep the upright position of the probe head 22. The probe head 22 in this position is not in contact with the holder body 31, except the rear end face of the probe head 22. Because of this, portions of the holder body 31 other than the bottom wall 46 can be removed. However, to protect the probe head 22 against the external force, to prevent the probe head 22 from falling in response to an excessive inclination force applied to the probe head 22, and to provide psychological security, for example, the holder body 31 may have a cup shape or a well shape.

Figure 7:
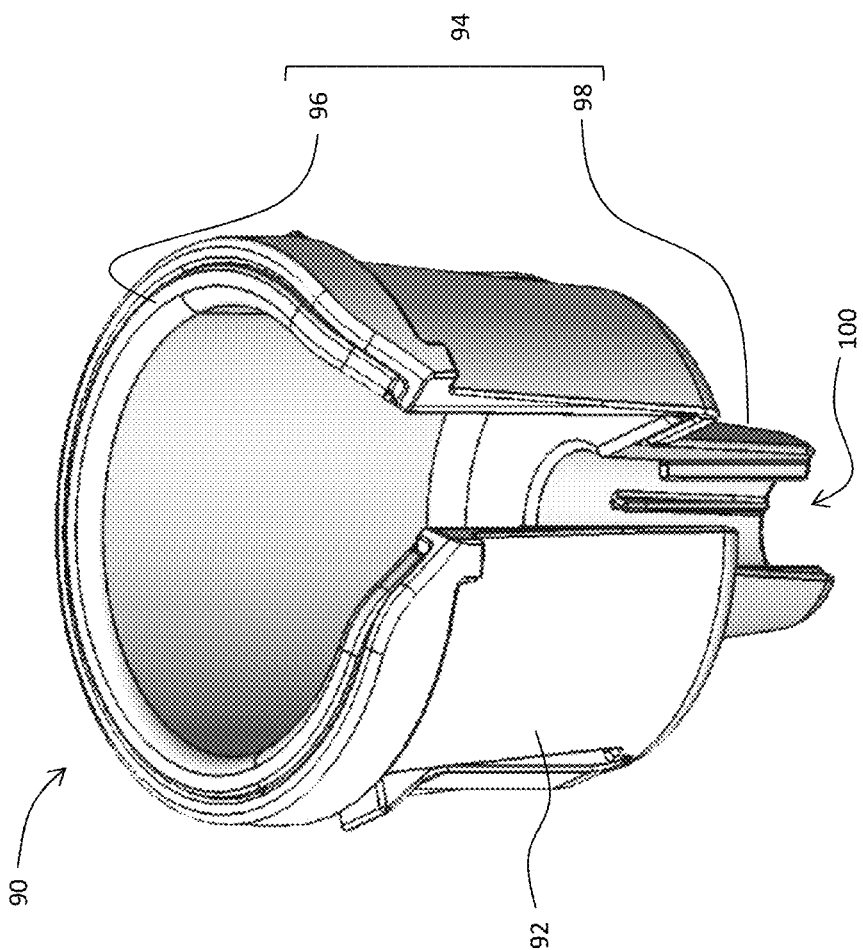
FIG. 7 is a perspective view illustrating a probe holder according to a modification example.

FIG. 7 illustrates a modification example probe holder. In comparison with the probe holder 20 illustrated in FIG. 3 and other drawings, a probe holder 90 in FIG. 7 has a rounded top portion and rounded ribs. However, the probe holder 90 illustrated in FIG. 7 and the probe holder 20 illustrated in FIG. 3 share a basic configuration.

The probe holder 90 includes a hard casing 92 and an elastic structure 94. The elastic structure 94 includes an inner cover 96 and a retainer unit 98. The retainer unit 98 includes, on its inner face, a rib array 100.

FIG. 8 is a front view of the probe holder 90, and FIG. 9 is a cross sectional view of the probe holder 90 taken along line A-A' in FIG. 8. As described above, the elastic structure 94 includes the inner cover 96 within the casing 92 and the retainer unit 98 protruding downward from the casing 92. The retainer unit 98 includes the rib array 100.

The probe holders according to the above embodiments do not hold the probe head itself but achieve a new holding method of holding the cable end extending from the probe head. This new method enables reliable holding of various probes by means of a simple configuration. In holding the probe, the probe head is mostly in a non-contact state, which is hygienic. Further, to remove the probe head out of the probe holder, two or more fingers can be easily inserted into a space around the probe head.

The probe holders according to the above embodiments include the elastic structure including a luminous material, which would result in a self-luminous elastic structure in a dark surrounding. This configuration increases visibility of the probe holder.

The invention claimed is:

1. A probe holder comprising:
    a holder body having a support face configured to support a rear end of a probe head that is in an upright position; and
    a retainer unit disposed under the holder body, the retainer unit configured to hold a cable end connecting to the rear end of the probe head in the upright position, the retainer unit including
        an enclosing wall protruding downward from the holder body, and
        a plurality of projections protruding from an inner face of the enclosing wall and being in elastic contact with an outer face of the cable end, and
    wherein the holder body includes an upper slit extending vertically, the upper slit being disposed for a cable to pass therethrough, and
    wherein the enclosing wall includes a lower slit extending vertically to connect to the upper slit, the lower slit being disposed for the cable to pass therethrough.

2. The probe holder according to claim 1, wherein the retainer unit is configured to hold a cable boot surrounding a cable body.

3. The probe holder according to claim 1, wherein
    the enclosing wall includes two edges that define the lower slit,
    the plurality of projections are a plurality of ribs extending vertically and protruding toward a center axis of the retainer unit, and
    the plurality of ribs that are the plurality of projections include two ribs disposed adjacent to the two edges, respectively.

4. The probe holder according to claim 1, wherein the holder body comprises:
    a hollow casing; and
    an inner cover having the support face and covering an inner face of the casing.

5. The probe holder according to claim 4, wherein the inner cover and the retainer unit are integral to form an elastic structure.

6. The probe holder according to claim 5, wherein the elastic structure includes a luminous material.

7. The probe holder according to claim 1, wherein at least one of the holder body or the retainer unit partially includes a luminous material.

* * * * *